(12) United States Patent
Mankovich et al.

(10) Patent No.: US 12,062,428 B2
(45) Date of Patent: *Aug. 13, 2024

(54) IMAGE CONTEXT AWARE MEDICAL RECOMMENDATION ENGINE

(71) Applicant: KONINKLIJKE PHILIPS N.V., Eindhoven (NL)

(72) Inventors: Gabriel Ryan Mankovich, Boston, MA (US); Lucas De Melo Oliveira, Melrose, MA (US); Ranjith Naveen Tellis, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/198,865

(22) Filed: May 18, 2023

(65) Prior Publication Data

US 2023/0368893 A1    Nov. 16, 2023

Related U.S. Application Data

(63) Continuation of application No. 15/767,532, filed as application No. PCT/IB2016/056301 on Oct. 20, 2016, now Pat. No. 11,664,111.

(60) Provisional application No. 62/248,642, filed on Oct. 30, 2015.

(51) Int. Cl.
| | |
|---|---|
| *G06F 3/0482* | (2013.01) |
| *G06T 7/00* | (2017.01) |
| *G16H 30/20* | (2018.01) |
| *G16H 30/40* | (2018.01) |
| *G16H 40/63* | (2018.01) |

(Continued)

(52) U.S. Cl.
CPC .......... *G16H 30/20* (2018.01); *G06F 3/0482* (2013.01); *G06T 7/0012* (2013.01); *G16H 30/40* (2018.01); *G16H 40/63* (2018.01); *G16H 50/20* (2018.01); *G16H 70/20* (2018.01); *G06F 2203/04804* (2013.01)

(58) Field of Classification Search
CPC ........ G16H 30/20; G16H 30/40; G16H 40/63; G16H 50/20; G16H 70/20; G06F 3/0482; G06F 2203/04804; G06F 3/048; G06T 7/0012

See application file for complete search history.

(56) References Cited

U.S. PATENT DOCUMENTS

| | | |
|---|---|---|
| 7,783,094 B2 | 8/2010 | Collins |
| 8,515,887 B2 | 8/2013 | Lord |
| 10,083,166 B2 | 9/2018 | Liu |

(Continued)

FOREIGN PATENT DOCUMENTS

| | | |
|---|---|---|
| EP | 1662415 A1 | 5/2006 |
| GB | 2436156 A | 9/2007 |

(Continued)

*Primary Examiner* — Sanchita Roy

(57) ABSTRACT

A system (100) for context aware medical recommendations includes a recommendation engine (138) and a user interface (122). The recommendation engine (138) identifies at least one suggested recommendation (140) according to a medical guideline and context in response to a first input indicating a finding (150) in a medical image (112) of a patient. The user interface (122) displays on a display device (120) the at least one suggested recommendation selectable as a second input.

20 Claims, 3 Drawing Sheets

(51) Int. Cl.
*G16H 50/20* (2018.01)
*G16H 70/20* (2018.01)

(56) References Cited

U.S. PATENT DOCUMENTS

| | | |
|---|---|---|
| 2004/0135824 A1 | 7/2004 | Fitzmaurice |
| 2004/0141010 A1* | 7/2004 | Fitzmaurice .......... G06F 3/0488 |
| | | 715/810 |
| 2005/0102315 A1 | 5/2005 | Krishnan |
| 2006/0274928 A1* | 12/2006 | Collins ................. G16H 30/40 |
| | | 382/132 |
| 2007/0175980 A1 | 8/2007 | Alsfadi |
| 2010/0280842 A1 | 11/2010 | Iwasa |
| 2011/0208540 A1 | 8/2011 | Lord |
| 2012/0106516 A1 | 3/2012 | Krishnan |
| 2013/0009860 A1 | 1/2013 | Kameda |
| 2014/0219500 A1* | 8/2014 | Moehrle ............... G06T 7/0014 |
| | | 382/103 |
| 2014/0337057 A1 | 11/2014 | Shibata |

FOREIGN PATENT DOCUMENTS

| | | |
|---|---|---|
| JP | 2005110944 A | 4/2005 |
| WO | 201531296 A1 | 3/2015 |
| WO | 2015092633 A1 | 6/2015 |

* cited by examiner

IMAGE CONTEXT AWARE MEDICAL RECOMMENDATION ENGINE

CROSS-REFERENCE TO PRIOR APPLICATIONS

This application is a Continuation of U.S. patent application Ser. No. 15/767,532 filed Apr. 11, 2028, which is the U.S. National Phase application under 35 U.S.C. § 371 of International Application No. PCT/IB2016/056301, filed on Oct. 20, 2016, which claims the benefit of U.S. Provisional Patent Application No. 62/248,642, filed on Oct. 30, 2015. These applications are hereby incorporated by reference herein.

FIELD OF THE INVENTION

The following generally relates to medical imaging and evaluation guidelines with specific application to healthcare practitioner review of electronically accessed medical images.

BACKGROUND OF THE INVENTION

Healthcare practitioners, such as radiologists, are called upon to review, evaluate, and make recommendations based on medical images of patients generated by scanners, such as X-ray Computed Tomography (CT), Magnetic Resonance (MR), Positron Emission Tomography (PET), Single Proton Emission Computed Tomography (SPECT), Ultrasound (US), combinations, and the like. Typically, images are generated by the scanner and stored in a storage system, such as a Picture Archiving and Communication System (PACS), departmental Radiology Information System (RIS), and the like and/or queued electronically for review by a qualified healthcare practitioner. Diagnostic imaging has seen dramatic increases in volume. For example, in an analysis of one large healthcare plan, cross section imaging rose from 260 examinations per 1000 plan enrollees in 1997 to 478 examinations per 1000 plan enrollees in 2006.

The healthcare practitioner reviews the image, evaluates the image for abnormalities, e.g. positive findings, and if abnormalities are found, typically makes annotations in the image, and then makes a recommendation concerning the patient. The recommendation is included in a report issued concerning the imaging examination, e.g. test results. The recommendation can be guided by a guideline given the context of the evaluation. The context includes a patient context, e.g. patient demographics, patient history, etc., an image context, e.g. anatomical location, type of image, contrast, type of study, etc., and a finding context, e.g. lesion, nodule, type of growth, etc.

Few guidelines are mandatory, such as Breast Imaging-Reporting and Data System (BI-RADS), which pertains to breast cancer guidelines. Many guidelines are optional, such as Fleischner Society recommendations for follow-up of small lung nodules. Some systems approach this with an optional user selection of a guideline after evaluating an image, which may not include a selected guideline. Recommendations can be based on the training of the healthcare practitioner, which may involve recommendations not based on any guideline or even consider a guideline.

Guidelines are constantly evolving as understandings about diseases change, and new guidelines are continuing to emerge. Education for healthcare practitioners is typically left to radiology departments and/or individual practitioners to understand and absorb changes in the guidelines, which can result in applying outdated guidelines or not applying a guideline. Guidelines provided in the context of a radiology system are typically provided as a selection prior to image evaluation.

Even assuming the healthcare practitioner is aware of current guidelines, identifying contextual information can be time-consuming and error prone. For example, in the Fleischner guidelines call for the contextual information which includes an age of the patient, the lung cancer risk factors for the patient, such as smoking, family history, exposure to second hand smoke, radon gas, asbestos, etc., presence or absence of prior lung nodules for the patient, the number of lung nodules in the current image, and the size of the lung nodules in the current image. Gathering this information typically means that the healthcare practitioner assembles the information accessing multiple different systems, which reduces efficiency and introduces chances of error. Plain text descriptions written from the assembled information have been shown to be frequently inaccurate or incomplete.

SUMMARY OF THE INVENTION

Aspects described herein address the above-referenced problems and others.

The following describes a method and system for a context aware recommendation concerning a patient, suggested to a healthcare practitioner reviewing a medical imaging examination. The context aware recommendation is according to a guideline selected in response to a finding and contextual information of the medical imaging examination.

In one aspect, a system for context aware medical recommendations includes a recommendation engine and a user interface. The recommendation engine identifies at least one suggested recommendation according to a medical guideline and context, in response to a first input indicating a finding in a medical image of a patient. The user interface displays on a display device at least one suggested recommendation selectable as a second input.

In another aspect, a method of context aware medical recommendations, includes identifying at least one suggested recommendation according to a medical guideline and context information in response to a first input identifying a finding in a medical image of a patient, and displaying at least one suggested recommendation on a display device selectable as a second input.

In another aspect, a system for context aware medical recommendations includes a context unit, a user interface, and a recommendation engine. The context unit determines context and generates a list of possible findings based on the context. The user interface displays on a display device the generated list of possible findings as a first input. The recommendation engine, in response to the first input indicating a finding of the possible findings in the medical image, identifies at least one suggested recommendation according to a medical guideline selected from a plurality of medical guidelines according to the determined context and the indicated finding. The determined context and the indicated finding include identification of at least one abnormality, an anatomical location of the identified at least one abnormality and at least one quantitative measure of the identified at least one abnormality. The user interface displays on the display device at least one suggested recommendation selectable as a second input.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1A:
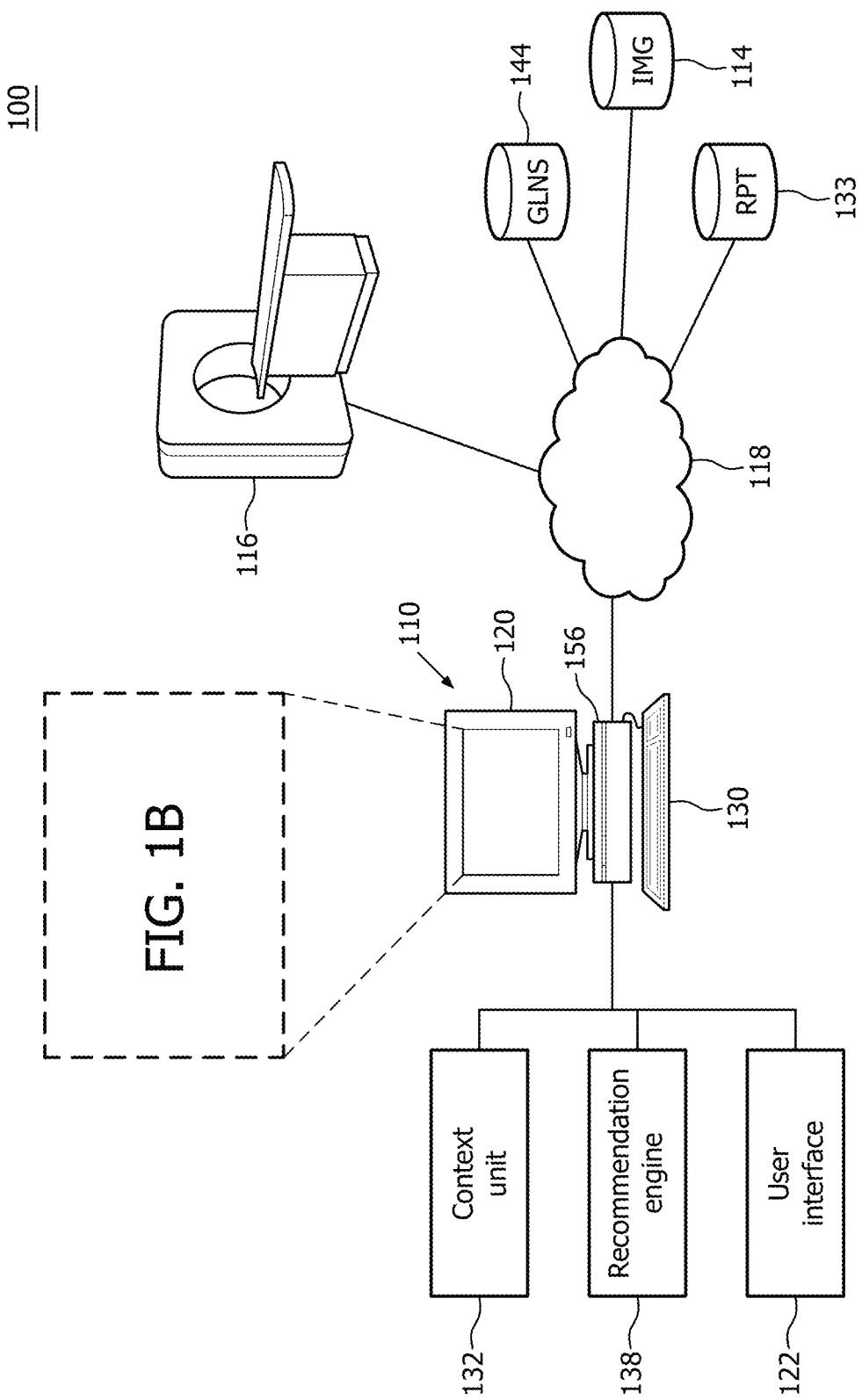
FIG. 1A schematically illustrates an embodiment of a context aware recommendation engine system.
Figure 1B:
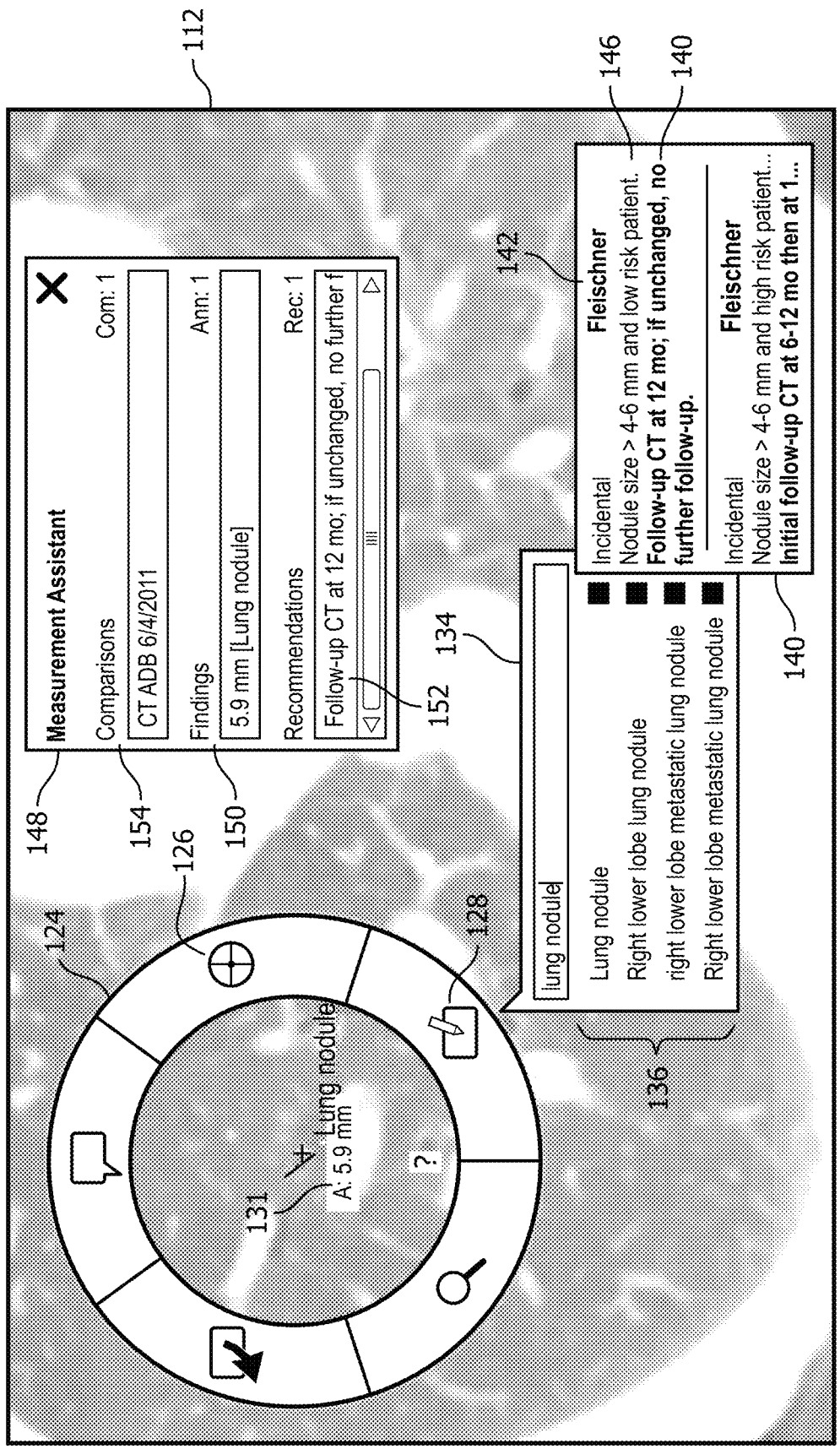
FIG. 1B schematically illustrates an example suggested recommendation of the context aware recommendation engine system in response to a finding and context of a medical imaging examination.

Initially referring to FIGS. 1A and 1B, an embodiment of a context aware recommendation engine system 100 is schematically illustrated. A computing device 110, such as a smartphone, laptop computer, desktop computer, tablet, body worn device, and the like, is configured to access, retrieve, or receive a medical image 112. The access can be local or remote. For example, the medical image 112 can be retrieved from local memory of the computing device 110, retrieve from a storage system 114, such as a Picture Archiving and Communication System (PACS), departmental Radiology Information System (RIS), a web portal, cloud storage, and the like, or retrieved directly from a scanner 116, such as a CT scanner, MR scanner, PET scanner, SPECT scanner, US scanner, and the like. The retrieval can include using a network 118, such as the Internet, intranet, public network, private network, combinations, and the like.

The medical image 112 is displayed on a display device 120 of the computing device 110 for review by a healthcare practitioner according to a user interface 122. The user interface 122 includes a menu, such as a ring menu 124 with a transparent center, e.g. medical image 112 visible through the center, and tool menus located around the ring shape. The tool menus include a measuring tool 126 and a findings tool 128. The visible center can be translated to and/or positioned around the region of interest or abnormality, such as a nodule, lesion, and the like. The healthcare practitioner interacts with the system through the user interface 122 using an input device 130, such as a touch screen, microphone, mouse, keyboard and the like.

The measuring tool 126, selected with an input, such as a mouse click, screen touch, and the like, generates a quantitative measurement of the abnormality 131, such as a distance measurement, volume measurement, area measurement, volume flow measurement, density measurement, and the like. For example, using a click and drag function with a mouse, a distance measure of the largest dimension of a lung nodule is made. The measuring tool 126 generates a label according to the measurement which includes a reference label, e.g. temporary name, such as an alphanumeric character, and the quantitative measurement. In the example shown in FIG. 1B, the label includes "A:" and "5.9 mm." The user interface can include displaying the information used to generate the measurement, such as a geometric shape indicative of the measured dimensions, e.g. a contrasted line, such as a dotted line for a distance measurement, a color and/or patterned contrasted area for an area measurement, and the like.

A context unit 132 determines context of the medical image 112. The context includes patient context, study context, and/or finding context. The patient context can include patient demographics, such as age, risk factors, and/or prior findings. For example, age can be obtained from metadata of the medical image 112, such as a DICOM header. Prior findings can be obtained from natural language processing (NLP) of reports 133 generated previously for the patient using NLP techniques known in the art. Study context can include a reason for the medical imaging examination, e.g. from the metadata and/or physician order requesting the medical imaging examination, relevant prior studies, e.g. prior medical images of the patient in a storage system 114 and/or reports 133 previously generated for the patient, imaging modality and anatomical location, e.g. obtained from medical image metadata. The finding context can include identification of the abnormality or finding type, e.g. nodule, measurement sizes, anatomical locations, image numbers and/or series types. For example, the context unit 132 determines the age of the patient from a DICOM header of the current medical image, determines a history of smoking and prior lung nodules from NLP of prior reports of the patient, and a nodule in the lung and size measurement corresponding to inputs from user interface 122.

The findings tool 128 receives an input indicative of the finding 134. The findings tool 128 can generate a list of possible finding 136 based on context from the context unit 132. For example, in the medical image 112 of a chest, the possible findings can be limited to those based on the anatomical location of the image, e.g. abnormalities of the chest, and/or based on the location of the ring menu 124 relative to a more specific anatomical location within the image, such as possible findings within a lower right lobe of the lung, e.g. displayed finding includes the anatomical location and identification of abnormality, e.g. nodule (undifferentiated), metastatic tumor, benign tumor. In one embodiment, the findings tool 128 includes the context of the measurement, which can include differences in measurements from prior medical imaging studies. For example, the context unit identifies a corresponding nodule in a prior imaging study of the patient, e.g. image registration and/or user input, and a change in size between the prior imaging study and the current imaging study is computed. Based on the change in size, the possible findings can be further limited, e.g. increase greater than a threshold amount is a lesion. In one embodiment, the list of possible finding types 136 is dynamically adjusted by the user interface 122. For example, as inputs are received, such as individual characters input via the input device 130, the list of possible finding 136 is character by character matched with the input to reduce displayed the possible finding 136.

A recommendation engine 138, in response to an input indicating the finding identifies a suggested recommendation 140 according to a medical guideline 142 and the context. The finding 134 with the context includes the identity or type of abnormality, the anatomical location and the quantified measurement 131. The recommendation engine 138 selects the medical guideline from a data store of medical guidelines 144 according to the context. For example, if the context includes the anatomical location of a breast, and a finding of a nodule or lesion, then the guideline selected is BI-RADS. In another example, if the anatomical location is the lung, and the finding is an incidental nodule, then the guideline selected is a Fleischner.

The data store of guidelines 144 can include mandatory and non-mandatory or optional guidelines. The data store of guidelines 144 can include computer storage, such as local or remote storage, cloud storage, distributed storage, and the like. The data store of guidelines 144 can include system, file, and/or database organization. The data store of guidelines 144 can include optimized access according to findings 134 including anatomical location and/or quantitative measurements 131. The data store of guidelines 144 can include optimized access according to other contextual information, such as patient demographics, type of imaging examination, risk factors, and the like.

The suggested recommendation 140 can include multiple suggested recommendations. In some instances this may be due to partial context information. For example, where the risk factors are determinable from the available information for a lung nodule of 5.9 mm, a suggested recommendation for a high risk patient and a second suggested recommendation for a low risk patient are displayed. In some instances, this may be due to different guidelines for the same finding and context.

The user interface 122 displays the suggested recommendation 140 or recommendations, which can be displayed as a selectable menu item. For example, in FIG. 1B, the selectable menu item is shown as a cascading drop down box. The displayed suggested recommendation 140 can include an identity of the guideline 142, e.g. Fleischner, BI-RADS, etc. The displayed suggested recommendation 140 can include a rule 146 which maps the finding 134 and context to the suggested recommendation 140. For example, a rule of finding type of lung nodule of 4-6 mm and low risk factors maps to a suggested Fleischner recommendation of "Follow-up CT at 12 months; if unchanged, no further follow-up."

The suggested recommendation 140 is selected in response to an input, such as a mouse click, voice command, screen touch change, and the like. The user interface 122 can include a response 148 which assembles the findings 150 and the selected recommendation 152. The response 148 can include other contextual information, such as a prior medical imaging examination 154, e.g. used for comparative measurements. The user interface 122 can generate a report of the imaging examination study including the displayed medical image 112. The generated report can be stored in the reports 133 and/or distributed electronically.

The user interface 122, the context unit 132, and the recommendation engine 138 comprise one or more configured processors 156, e.g., a microprocessor, a central processing unit, a digital processor, and the like) are configured to execute at least one computer readable instruction stored in a computer readable storage medium, which excludes transitory medium and includes physical memory and/or other non-transitory medium. The processor 156 may also execute one or more computer readable instructions carried by a carrier wave, a signal or other transitory medium. The processor 156 can include local memory and/or distributed memory. The processor 156 can include hardware/software for wired and/or wireless communications. For example, the lines indicate communications paths between the various components which can be wired or wireless. The processor 156 can comprise the computing device 110.

Figure 2:
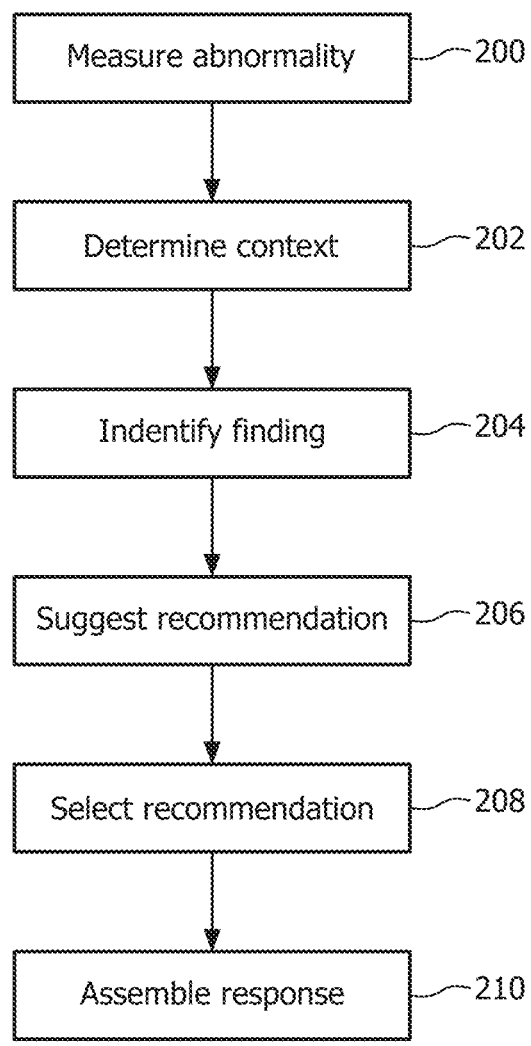
FIG. 2 flowcharts an embodiment of suggesting a contextually aware recommendation.

With reference to FIG. 2, an embodiment of suggesting a contextually aware recommendation is flowcharted. At 200, an identified abnormality in a displayed medical image 112 of a patient can be measured. The measuring can include a distance, an area, a volume, a rate, a density, combinations, and the like of aspects of the abnormality. The measurement can be received from an input and/or determined from the medical image based on the input.

At 202, context is determined, which can include patient context, image context and/or finding context. The context can be determined from information stored in the metadata of the medical image 112, prior images and/or prior examinations of the patient, and/or direct entry.

At 204, a finding is identified. The finding includes a type of abnormality in the medical image 112. The finding includes the measurement. The identification of a finding can be in response to an input indicative of the abnormality selected from a list of possible findings. The displayed list of possible findings can be limited by the context, e.g. findings possible according to the anatomical location, imaging modality, type of imaging examination, measurement, and/or measurement type, and the like.

In response to an input selecting the finding or inputting the finding, one or more suggested recommendations for the patient are displayed at 206. The one or more suggested recommendations are according to one or more medical guidelines selected according to the finding and the context. The medical guidelines can include mandatory and/or non-mandatory guidelines. The suggested recommendations are selected according to a rule which maps the finding and the context to a guideline or guidelines and suggested recommendations within a guideline. The displayed suggested recommendation can include identification of the guideline. The displayed suggested recommendation can include the rule used to determine the suggested recommendation. The displayed suggested recommendations can include partial context, which satisfies only part of the rule.

At 208, an input selects one of the displayed suggested recommendations for the patient as a recommendation. At 210, a response is assembled which includes the recommendation and the findings. The response can include information determined from the context, such as prior imaging examinations, specific images, prior measurements, and/or determined risk factors and their sources. A report can be generated from the assembled response, which in some instances is a result of reading the imaging examination. The response can be assembled as each portion is obtained. For example, as context information is identified, such as prior imaging examinations, reference information can be included in the display. As each finding is made, the assembled display is updated. The assembled display is updated as the recommendation is selected from the suggested recommendations.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A system for context aware evaluation, comprising:
   a display device configured to display a user-identified medical image of a subject and a user-positionable menu over a sub-portion of the user-identified medical image, wherein the user-positionable menu includes a findings tool and a measurement tool;
   an input device configured to receive a first user input identifying a location of a finding in a region of interest within the sub-portion with the measurement tool while the menu is displayed over the sub-portion and invoking the measurement tool to take a measurement of the finding;
   a context unit configured to determine a context of the evaluation including at least one of a context of the subject, a context of an imaging study producing the displayed user-identified medical image including an anatomical region of the sub-portion, and a context of the finding including the measurement and an anatomical location of the finding;
   wherein the input device is further configured to receive a second user input identifying a type of the finding from a displayed list of types of possible findings for the region of interest with the findings tool, wherein the findings tool generates the list based on the context of the evaluation; and a recommendation engine configured to identify multiple recommended actions for the finding based on a medical guideline for the type of the finding and the context of the evaluation, and display the multiple recommended actions in a recommendation window.

2. The system according to claim 1, wherein the finding includes identification of at least one abnormality, an anatomical location of the identified at least one abnormality and at least one quantitative measure of the identified at least one abnormality.

3. The system according to claim 1, wherein the recommendation engine identifies the medical guideline from a plurality of medical guidelines based on the-context of the evaluation, the identified medical guideline indicates a follow up action for the type of the finding for the region of interest, and a recommended action includes the follow up action from the identified medical guideline.

4. The system according to claim 3, wherein the follow up action is an examination within a predetermined time period.

5. The system according to claim 1, wherein each recommended action of the multiple recommended actions includes an identification of the guideline and a rule which maps the finding and the context of the evaluation to the respective recommended action.

6. A method of context aware medical recommendations, comprising:
displaying a medical image of a subject from an examination;
superimposing a user-positionable menu over a sub-portion of the displayed medical image, wherein the user-positionable menu includes a findings tool and a measurement tool;
receiving an input that invokes the measurement tool to generate a measurement of tissue of interest in the sub-portion of the medical image;
identifying an anatomical location of the tissue of interest from the anatomy in the medical image based on a user input received while the user-positionable menu is displayed over the sub-portion;
determining a context for the examination based on the measurement and the anatomical location;
displaying a list of types of findings based on the context;
receiving a first input identifying a type of a finding from the displayed list of types of findings;
displaying a list of predetermined recommended actions for a finding in a recommendation window based on the type of the finding, a medical guideline for the type of the finding, and the context; and
receiving a second input identifying at least one recommended action from the list of the predetermined recommended actions.

7. The method according to claim 6, wherein the finding includes identification of at least one abnormality, an anatomical location of the identified at least one abnormality and at least one quantitative measure of the identified at least one abnormality.

8. The method according to claim 6, further including identifying the medical guideline, wherein identifying the medical guideline includes selecting a medical guideline from a plurality of medical guidelines based on the context, and the plurality of medical guidelines includes at least the Fleischner Society medical guideline and the Breast Imaging-Reporting and Data System medical guideline.

9. The method according to claim 6, wherein the identified medical guideline is a non-mandatory medical guideline or optional medical guideline.

10. The method according to claim 6, wherein determining the context includes using information retrieved from at least one of:
metadata corresponding to the medical image or patient information obtained from natural language processing of prior reports about the subject.

11. The method according to claim 6, wherein the at least one recommended action includes limiting a plurality of recommended actions according to the context.

12. The method according to claim 6, wherein identifying the guideline includes mapping the finding and the context to the suggested at least one recommended action according to a rule.

13. The method according to claim 6, wherein the user-positionable menu includes a transparent sub-region, and a portion of the displayed user-identified medical image behind the user-positionable menu is visible through the transparent sub-region, and further including:
positioning the user-positionable menu about a region of interest in the displayed user-identified medical image such that the region of interest is visible through the transparent sub-region and based on a user input.

14. The method according to claim 13, wherein the user-positionable menu includes an opaque ring shaped region surrounding the transparent sub-region.

15. The method according to claim 14, wherein the findings tool and the measurement tool are located at different arc segments of the user-positionable menu.

16. The method according to claim 11, further including:
taking a quantitative geometric measurement of the finding in the region of interest with the measurement tool;
displaying a label identifying a type of the quantitative geometric measurement and a numerical value of the quantitative geometric measurement in connection with the finding; and
displaying a summary window with the type of finding, a user selected sub-set of the list of the predetermined recommended actions, and a value of the measurement.

17. A non-transitory computer readable medium encoded with computer executable instructions, which, when executed by a processor of a computing system, causes the processor to:
display a user-identified medical image of a subject;
superimpose a user-positionable menu over a sub-portion of the displayed user-identified medical image, wherein the user-positionable menu includes a findings tool configured to identify a type of a finding and a measurement tool configured to take a measurement of the finding and a transparent sub-region;
position the user-positionable menu about a region of interest in the displayed user-identified medical image such that the region of interest is visible through the transparent sub-region and based on a user input;
identify a location of a finding of interest in the region of interest with the measurement tool based on a user input received while the user-positionable menu is displayed over the sub-portion;
receive an input identifying the type of a finding from a displayed list of types of possible findings for the region of interest with the findings tool;
determine a context including at least one of a context of the subject, a context of an imaging study producing the displayed user-identified medical image, and a context of the finding;

identify a list of predetermined recommended actions for the finding according to the type of the finding, a medical guideline for the type of the finding, and the at least one context, wherein the medical guideline includes a measurement range and a risk for the type of the finding;

display the list of predetermined recommended actions in a recommendation window; and receive an input identifying at least one recommended action from the list of the predetermined recommended actions in the recommendation window.

18. The non-transitory computer readable medium of claim 17, wherein the computer executable instructions further cause the processor to:

take a quantitative geometric measurement of the finding in the region of interest with the measurement tool;

display a label identifying a type of the quantitative geometric measurement and a numerical value of the quantitative geometric measurement in connection with the finding; and display the value of the measurement in a transparent sub-region of the user-positionable menu, which is surrounded by an opaque ring shaped region of the user-positionable menu.

19. The system according to claim 1, wherein a summary window is displayed and includes an identification of a prior medical imaging examination used for comparative measurements.

20. The system according to claim 1, wherein a summary window is displayed with only a user selected recommended action mary.

* * * * *